United States Patent [19]

Goodall et al.

[11] 4,252,987
[45] Feb. 24, 1981

[54] DIMERIZATION OF 1-ALKENES

[75] Inventors: Brian L. Goodall; Harry van der Heijden, both of Amsterdam, Netherlands

[73] Assignee: Shell Oil Company, Houston, Tex.

[21] Appl. No.: 123,871

[22] Filed: Feb. 22, 1980

[30] Foreign Application Priority Data

Mar. 2, 1979 [GB] United Kingdom ................. 7546/79

[51] Int. Cl.$^3$ .............................................. C07C 2/24
[52] U.S. Cl. .................................... 585/513; 585/527; 585/532
[58] Field of Search ........................ 585/513, 527, 532

[56] References Cited

U.S. PATENT DOCUMENTS

| 3,564,071 | 2/1971 | Izawa et al. | 585/512 |
| 3,879,485 | 4/1975 | Belov et al. | 585/513 |
| 3,969,429 | 7/1976 | Belov et al. | 585/513 |

*Primary Examiner*—Curtis R. Davis

[57] ABSTRACT

Dimerization of alpha,beta-unsubstituted 1-alkenes, having at least three carbon atoms, in the presence of a catalyst comprising
(a) a titanium-containing component of the formula $Cp_2TiXY$, 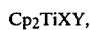

wherein Cp represents an optionally alkyl-substituted cyclopentadienyl group, X represents a halogen atom or an alkyl group, and Y represents a halogen atom,
(b) an alkylaluminum halide, and
(c) a nitrogen Lewis base, is characterized by high reaction selectivity to certain dimer products and little formation of higher polymers.

14 Claims, No Drawings

DIMERIZATION OF 1-ALKENES

BACKGROUND OF THE INVENTION

The invention relates to a process for the catalytic dimerization of one or more alpha,beta-unsubstituted 1-alkenes having at least three carbon atoms.

Dimerization of alkenes is generally well known in the chemical arts. Under suitable reaction conditions and in the presence of recognized catalysts, one alkene molecule adds to another to form a dimer molecule, which is itself an alkene. Dimerization reactions have commercial utility in the production of chemicals for any number of end uses, for example, in the preparation of high-octane gasoline components or in the synthesis of intermediates in detergent manufacture.

In the preparation of olefin dimers it is most often desirable that the dimerization reaction be selective with regard to formation of dimer product species, and also that formation of polymer by-product in the reaction mixture be minimized. Yet, it is recognized that prior art dimerization procedures are generally characterized by the production of a reaction mixture comprising a substantial amount of higher polymers of the alkene starting material and, in the case of alkenes having three or more carbon atoms, comprising a significant quantity of each of a number of possible dimer product isomers. Thus, for example, when ethylene and/or propylene are dimerized, according to the process of U.S. Pat. No. 3,564,071, in the presence of a complex catalyst consisting of an organo-aluminum compound and an alkyltitanate, the product mixture contains a significant amount of a solid polymer. Furthermore, the reaction of propylene alone according to this patent is shown to have low selectivity to the formation of any of the several possible $C_6$ dimer species. Likewise, the procedures of Great Britain Patent 896,822 for dimerization of alkenes in the presence of an aluminum dialkyl halide result in a broad range of product dimers and polymers. Similar results are shown in Great Britain Pat. No. 1,058,680 for the reaction of olefins over catalysts comprising certain alkyl metal or allyl metal halide compounds.

Great Britain Pat. No. 840,028 discloses a propylene dimerization process which is shown to be more selective to the production of the single 2-methyl-pentene-1 product when operated in the presence of a catalyst comprising a trialkyl-aluminum and either nickel or platinum. However, the selective results illustrated by this patent are obtained at relatively severe reaction conditions, e.g., a temperature of approximately 250° C. and a pressure of about 120 atmospheres, or, equivalently, about 12,000 kilopascals (kPa). Even more severe conditions, e.g., a temperature exceeding 250° C. and a pressure in the range of 225 to 400 atmospheres, are specified for the dimerization of olefins in the presence of organo-aluminum compounds according to the process of Great Britain Pat. 853,187.

SUMMARY OF THE INVENTION

It has now been found that alpha,beta-unsubstituted 1-alkenes having three or more carbon atoms can advantageously be dimerized under moderate process conditions in the presence of a particularly specified three-component catalyst mixture. Dimerization according to the invention includes both dimerization in the pure sense, e.g., the reaction between two like alkene molecules, as well as what is commonly referred to as co-dimerization, e.g., the reaction between two different alpha,beta-unsubstituted 1-alkenes.

The dimerization process of the invention is necessarily carried out in the presence of a catalyst comprising
(a) a titanium-containing component of the formula $Cp_2TiXY$, wherein Cp represents a cyclopentadienyl group or an alkylsubstituted cyclopentadienyl group, X represents a halogen atom or an alkyl group, and Y represents a halogen atom,
(b) an alkylaluminum halide, and
(c) a nitrogen Lewis base. The catalyst component described as a nitrogen Lewis base is herein specified to include any Lewis base which derives its basic character from the presence of one or more nitrogen atoms having an unshared electron pair.

The dimerization of alpha,beta-unsubstituted 1-alkenes in the presence of the above-specified catalyst proceeds with high selectivity according to the equation

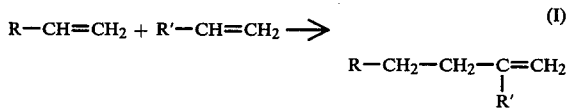

$$R-CH=CH_2 + R'-CH=CH_2 \longrightarrow \qquad (I)$$
$$R-CH_2-CH_2-\underset{\underset{R'}{|}}{C}=CH_2$$

where R and R' represent the same or different alkyl groups. Thus, for example, propylene is dimerized to substantially the single product 2-methyl-1-pentene, and a mixture of propylene and 1-butene is dimerized in high selectivity to a mixture of the four products 2-methyl-1-pentene, 2-ethyl-1-hexene, 2methyl-1-hexene and 2-ethyl-1-pentene.

DESCRIPTION OF THE PREFERRED EMBODIMENTS

The instant invention is seen as an improvement upon prior art processes for the dimerization of alpha,beta-unsubstituted 1-alkenes. Specifically, said improvement is believed to reside in the use of a particular critical combination of the three catalyst components listed above.

With regard to the titanium-containing component of the catalyst, it has been found suitable for purposes of the invention to use such components wherein X represents a halogen atom or an alkyl group and Y represents the same or a different halogen atom. When the component is one in which X represents an alkyl group, it has been observed that lower overall dimerization catalyst activity is generally to be expected for a use of an alkyl group having more than about five carbon atoms, in comparison to the activity of components in which X is a lower alkyl group. Accordingly, when X represents an alkyl group preference is given to alkyl groups having no more than about five carbon atoms, e.g. methyl, ethyl, n-propyl or iso-pentyl. It can also be said that as a general matter components in which X represents a halogen atom are to be preferred over those in which it represents an alkyl group. Each of the X and Y substituents is suitably then either the same or different halogens. Fluorine, chlorine, bromine, and iodine are preferred for this purpose. Most preferred are components in which both X and Y represent the same halogen, particularly those in which both are chlorine. The two cyclopentadienyl (Cp) substituents of this titanium-containing catalyst component are themselves each individually optionally substituted with one or more alkyl groups. Thus, Cp may suitably represent cyclopentadienyl or a cyclopentadienyl derivative in which the hydrogen atom on one or more of the ring carbon members is replaced by, for instance, methyl, ethyl, or propyl. Alkyl-substitution of the cyclopentadienyl group is not found to significantly influence catalyst dimerization activity. A most preferred titanium-containing catalyst component is di(cyclopentadienyl)titanium dichloride.

With regard to the alkylaluminum halide catalyst component for use in the process of the invention, compounds heretofore employed as catalysts in dimerization and polymerization reactions are generally suitable. Illustrative examples of this component include alkylaluminum dihalides, such as methyl- and ethylaluminum dichloride, dialkylaluminum halides, such as dimethyl- and diethylaluminum chloride, and trialkyldialuminum trichlorides, such as dimethyl- and diethylaluminum chloride. For alkyl substituents of this catalyst component, ethyl and methyl groups are preferred, while ethyl groups are considered most preferred. Special preference is given to the use of ethylaluminum dichloride.

It has been found that the presence of a nitrogen Lewis base catalyst component, that is, a Lewis base which derives its basic character from the presence of one or more nitrogen atoms having unshared electron pairs, is critical to the selective dimerization of alpha,-beta-unsubstituted 1-alkenes according to the process of the invention. The presence of such a Lewis base in the dimerization reaction process of the invention is a critical factor in preventing or substantially reducing the formation of higher polymer which would be produced as a reaction by-product in the absence of this catalyst component. For purposes of the invention, the nitrogen Lewis base may be a cyclic or acyclic, aliphatic, aromatic, or heterocyclic compound having the specified nitrogen atom with at least one unshared electron pair. By way of example, and without intention to limit the invention, it may be said that compounds suitable for this service include amines, such as propylamine, aniline, xylidene, diethylenetriamine, pyridine, naphthylamine, benzylamine, etc., imines, such as cyclohexanimine, p-benzoquinone diimine, hexamethylenimine, benzylidenimine, etc., and nitriles, such as butyronitrile, benzonitrile, etc. The amines form a preferred general class of nitrogen Lewis bases; tertiary amines, such as for instance triethylamine, triethylenediamine, dimethylcyclohexylamine and benzyldimethylamine, are a particularly preferred class. While no criticality is assigned to the number of carbon atoms in an organic nitrogen Lewis base component, it has been found desirable that the component have less than about 20 carbon atoms; most desirably, it has between about 4 and 12 carbon atoms. The bridged heterocyclic amine derivative 1,4-diazabicyclo(2.2.2)octane is generally considered most preferred for use in the practice of the invention.

For purposes of the invention, it is contemplated that the dimerization reaction be carried out in a liquid solution comprising the above described catalyst combination and one or more alpha,beta-unsubstituted 1-alkene reactants. Although the amount of catalyst contained in the solution is not critical to process performance, it is to be noted that in general dimerization proceeds faster at higher catalyst concentrations. With specific regard to the catalyst's titanium component, while very small quantities, e.g., 0.05 millimol per mol of alpha,beta-unsubstituted 1-alkene, can suitably be used, it is preferred that there be at least 0.5 millimol per mole of alkene reactant in the reaction mixture. Preference is given to this larger quantity of this component both because of its influence upon reaction rate and furthermore because it is observed that a portion of the titanium component may be reduced and lose catalytic activity under prevailing dimerization reaction conditions. There is believed to be no additional advantage in the use of more than about 10 millimol of titanium component per mole of alkene reactant. With regard to the alkylaluminum halide component of the catalyst combination, it is normally desirable that there be an excess of this component over the molar concentration of the titanium component in the dimerization reaction mixture. Preferably, the molar ratio of the aluminum component to the titanium component is at least about 4. Since at very high aluminum to titanium component ratios, the alkylaluminum halide may function to reduce the titanium component, preference is also given to the use of aluminum to titanium component ratios of less than about 20. Most preferably, this ratio is between about 10 and 15. The nitrogen Lewis base is typically used in the reaction mixture in such an amount that the molar ratio of the nitrogen base to the alkylaluminum component is at least about 0.1. In order to realize full benefit from the presence of the Lewis base in the dimerization catalyst combination it is usually not necessary to employ a molar ratio greater than 1.0, although still higher ratios can be suitably used. A molar ratio of the nitrogen Lewis base component to the alkylaluminum halide component in the range of about 0.2 to 0.5 is generally most preferred.

The process of the invention, employing the above-described catalyst combination, is useful for the dimerization in high selectivity of alpha, beta-unsubstituted 1-alkenes having at least three carbon atoms. Alpha,-beta-unsubstituted 1-alkenes having up to 25 carbon atoms are particularly suitable reactants in the invention, and those having between about 3 and 10 carbon atoms, inclusive, are preferred. Linear and branched alkenes are both suitable reactants. Exemplification of linear 1-alkenes which can be dimerized according to the invention is provided by the homologous alkene series of propylene, 1-butene, 1-pentene, etc. Examples of suitable branched alkenes include 3-methyl-1-butene, 3-methyl-1-pentene, and 4-methyl-1-pentene.

The process of the invention may be applied to dimerization in a reaction mixture containing either a single alpha,beta-unsubstituted 1-alkene or multiple alpha,beta-unsubstituted 1-alkene compounds. The presence in the reaction mixture of more than one such 1-alkene species does not substantially interfere with the selectivity of the reaction in the mixture of two like 1-alkenes to essentially a single product according to equation (I) above, or with the ability of the invention to minimize formation of higher polymer by-products, although it does lead to production of "co-dimers" upon reaction between the various difference 1-alkene compounds of the mixture. Such co-dimerization may also be characterized as having enhanced selectivity to certain specific co-dimer product species.

To increase contact in solution between the alkene reactant and the catalyst combination for purposes of the invention, it has been found desirable to utilize an organic reaction solvent. The particular nature of the solvent is not critical to the invention—various common solvents which are essentially inert to the catalyst, such as for instance saturated aliphatic or aromatic hydrocarbons and aliphatic or aromatic ethers, may suitably be used. Halogenated aromatic hydrocarbons, which generally have a high degree of solubility for the catalyst components and which have no noticeable tendency to react with either the catalyst or the alkene reactant, are particularly preferred solvents; bromobenzene and chlorobenzene are most preferred. The optimal amount of reactant solvent to be utilized in practice of the invention will depend, of course, upon the particular nature of the alkene and the catalyst components in the reaction mixture and upon the reaction conditions employed in any given dimerization process according to the invention. It may be said, however, that reaction solvent will generally best be used in an amount such that the relative molar ratio of solvent to alkene reactant is between about 0.1 and 10.

The dimerization reaction process of the invention can very suitably be carried out at any temperature between about 0° C. and 80° C. Somewhat higher and lower temperatures, for example, between about −10° C. and 100° C., can also be used, provided the various catalyst components and the reactants remain in solution in specified quantity in the dimerization reaction mixture. Preference is generally given to process temperatures between about 10° C. and 40° C. Operating pressure is not a critical factor in carrying out the process of the invention. When low boiling point alpha,-beta-unsubstituted 1-alkenes, for instance propylene or 1-butene, are used as reactants, superatmospheric pressures are typically encountered during process operation. For practical reasons, preference is generally given to operation between atmospheric pressure and about 1000 kPa. Pressures between atmospheric and 500 kPa are most preferred.

It has been observed that the process of the invention is most suitably carried out in the absence of air and moisture which tend to cause degradation of the catalyst. Maintaining an inert gas, such as nitrogen, helium or argon, above the liquid reaction solution aids in the desired exclusion of air and water.

Dimerization of alpha,beta-unsubstituted 1-alkenes according to the invention is further illustrated by the following examples.

EXAMPLE I

To a 30 ml glass bottle, maintained under nitrogen atmosphere, were added 10 milligrams (0.04 millimol) of di(cyclopentadienyl)titanium dichloride, 13 milligrams (0.12 millimol) of 1,4-diazabicyclo(2.2.2)octane, and then 15 ml of bromobenzene. The resulting solution was then saturated with propylene, after which 0.062 ml (0.6 millimol) of ethylaluminum dichloride was added to the solution. Finally, propylene pressure was raised to 200 kPa.

After a reaction of 90 minutes at 25° C., the yield of dimer product was 0.80 millimol. Analysis of this dimer by gas chromatography indicated that it was substantially the single compound 2-methyl-1-pentene.

EXAMPLE 2

To a 30 ml glass bottle, under an argon atmosphere, were added 5 milligrams (0.02 millimol) of di(cyclopentadienyl)titanium dichloride, 6.7 milligrams (0.06 millimol) of 1,4-diazabicyclo(2.2.2)-octane, 4.3 ml (34.4 millimol) of 1-hexene, 6 ml of bromobenzene, and finally 0.031 ml (0.3 millimol) of ethyl aluminum dichloride.

After a reaction of 5.5 hours at 25° C., the dimer yield was 2.5 millimol, corresponding to an alkene conversion of 14.5 percent. Analysis by gas chromatography indicated that the dimer product was substantially the single compound 2-butyl-1-octene.

COMPARATIVE EXAMPLE

The product of Example 2 were repeated, but, for comparative purposes, without the addition of the 1,4-diazabicyclo(2.2.2)octane nitrogen Lewis base to the reaction mixture. The resulting product contained an unacceptably large amount of higher polymers.

EXAMPLE 3

To a 30 ml glass bottle, under an argon atmosphere, were added 8 milligrams (0.029 millimol) of bis(methylcyclopentadienyl)titanium dichloride, 11 milligrams (0.10 millimol) of 1,4-diazabicyclo(2.2.2)-octane, 5 ml (40 millimol) of 1-hexene, 7 ml of chlorobenzene and finally 0.045 ml (0.44 millimol) of ethylaluminum dichloride. After a reaction of 19.5 hours at 25° C., there had been formed 1.57 millimol of 2-butyl-1-octene.

EXAMPLE 4

To a 30 ml glass bottle, under an argon atmosphere, were added 7.2 milligrams (0.029 millimol) of di(cyclopentadienyl)titanium dichloride, 8 mg (0.072 millimol) of 1,4-diazabicyclo(2.2.2)octane, 5 ml (40.0 millimol) of 4-methyl-1-pentene, 7 ml of chlorobenzene, and 0.045 ml (0.44 millimol) of ethylaluminum dichloride. After a two hour reaction at 25° C., there had been formed 1.08 millimol of 2-isobutyl-6-methyl-1-heptene.

EXAMPLE 5

Under the general procedures of Examples 1-4, if a mixture of propylene and 1-butene were dimerized in solution in a chlorobenzene solvent and in the presence of bis(methylcyclopentadienyl)titanium dichloride, triethylenediamine, and methylaluminum dichloride, the dimer reaction product would be substantially the four compounds 2-methyl-1-pentene, 2-ethyl-1-hexene, 2-methyl-1-hexene, and 2-ethyl-1-pentene.

We claim as our invention:

1. A process for the selective dimerization of one or more alpha,beta-unsubstituted 1-alkenes having at least three carbon atoms by reaction in liquid solution and in the presence of a catalyst comprising (a) a titanium-containing component of the formula $$Cp_2TiXY,$$

wherein Cp represents an optionally alkyl-substituted cyclopentadienyl group, X represents a substituent selected from the class consisting of halogen atoms and alkyl groups, and Y represents a halogen atom, (b) an alkylaluminum halide, and (c) a nitrogen Lewis base, with the provision that the liquid solution contain at least about 0.05 millimol of the titanium-containing component per mol of alpha, beta-unsubstituted 1-alkene, with the provision that the solution comprise the alkylaluminum halide in molar excess over the titanium-containing component, and with the provision that the solution contain a quantity of the nitrogen Lewis base such that the molar ratio of nitrogen Lewis base to the alkylaluminum halide is at least about 0.1.

2. The process of claim 1, wherein the temperature of the liquid solution is between about 0° C. and 80° C.

3. The process of claim 2, wherein the titanium-containing component of formula Cp$_2$TiXY has as its substituent X a component selected from the class consisting of a chlorine atom and alkyl groups of one to five carbon atoms, and as its substituent Y a chlorine atom.

4. The process of claim 2, wherein the alkylaluminum halide is an ethylaluminum halide.

5. The process of claim 2, wherein the nitrogen Lewis base is tertiary amine.

6. The process of claim 3, wherein the alkylaluminum halide is an ethylaluminum halide and the nitrogen Lewis base is a tertiary amine.

7. The process of claim 3, wherein the titanium-containing component is dicyclopentadienyltitanium dichloride.

8. The process of claim 4, wherein the alkylaluminum halide is ethylaluminum dichloride.

9. The process of claim 5, wherein the nitrogen Lewis base is 1,4-diazabicyclo(2.2.2)octane.

10. The process of claim 2, wherein the solution contains at least about 0.5 millimol of titanium-containing component per mol of alpha,beta-unsubstituted 1-alkene.

11. The process of claim 10, wherein the catalyst has a molar ratio of alkylaluminum halide to titanium-containing component in the range of about 4 to 20.

12. The process of claim 11, wherein the molar ratio of alkylaluminum halide to titanium-containing component is in the range of about 10 to 15.

13. The process of claim 11, wherein the catalyst has a molar ratio of nitrogen Lewis base to alkylaluminum halide in the range of about 0.2 to 0.5.

14. The process of claim 2, wherein the temperature of the liquid solution is between about 10° C. and 40° C.

* * * * *